US007494811B2

(12) United States Patent
Wolfinbarger, Jr. et al.

(10) Patent No.: US 7,494,811 B2
(45) Date of Patent: Feb. 24, 2009

(54) IN VITRO GROWTH OF TISSUES SUITABLE TO THE FORMATION OF BONE AND BONE FORMING TISSUE FORMED THEREBY

(75) Inventors: Lloyd Wolfinbarger, Jr., Norfolk, VA (US); XiaoFei Qin, Virginia Beach, VA (US)

(73) Assignee: LifeNet Health, Virginia Beach, VA (US)

( * ) Notice: Subject to any disclaimer, the term of this patent is extended or adjusted under 35 U.S.C. 154(b) by 94 days.

(21) Appl. No.: 10/835,529

(22) Filed: Apr. 30, 2004

(65) Prior Publication Data

US 2005/0002910 A1  Jan. 6, 2005

Related U.S. Application Data

(60) Provisional application No. 60/466,772, filed on May 1, 2003.

(51) Int. Cl.
*C12N 5/00* (2006.01)
*C12N 5/02* (2006.01)
*C12N 5/04* (2006.01)

(52) U.S. Cl. .................. 435/373; 435/375; 435/377; 435/383; 435/384

(58) Field of Classification Search .......... 435/373, 435/375, 377, 383, 384
See application file for complete search history.

(56) References Cited

U.S. PATENT DOCUMENTS

| 4,485,097 | A | 11/1984 | Bell |
| 4,553,272 | A | 11/1985 | Mears |
| 4,963,489 | A | 10/1990 | Naughton et al. |
| 5,073,373 | A | 12/1991 | O'Leary et al. |
| 5,284,655 | A | 2/1994 | Bogdansky et al. |
| 5,290,558 | A | 3/1994 | O'Leary et al. |
| 5,298,254 | A | 3/1994 | Prewett et al. |
| 5,314,476 | A | 5/1994 | Prewett et al. |
| 5,405,390 | A | 4/1995 | O'Leary et al. |
| 5,484,601 | A | 1/1996 | O'Leary et al. |
| 5,507,813 | A | 4/1996 | Dowd et al. |
| 5,510,396 | A | 4/1996 | Prewett et al. |
| 5,531,791 | A | 7/1996 | Wolfinbarger, Jr. |
| 5,634,879 | A | 6/1997 | Mueller-Glauser et al. |
| 5,820,581 | A | 10/1998 | Wolfinbarger, Jr. |
| 5,843,182 | A | 12/1998 | Goldstein |
| 5,855,617 | A | 1/1999 | Orton |
| 5,899,936 | A | 5/1999 | Goldstein |
| 5,948,426 | A | * | 9/1999 | Jefferies ................. 424/423 |
| 6,372,257 | B1 | 4/2002 | Marchosky |
| 6,416,995 | B1 | 7/2002 | Wolfinbarger, Jr. |
| 6,458,375 | B1 | 10/2002 | Gertzman et al. |
| 2003/0144743 | A1* | 7/2003 | Edwards et al. .......... 623/23.63 |

OTHER PUBLICATIONS

Mizuno et al., "Three-dimensional composite of demineralized bone powder and collagen for in vitro anaylsis of chondroinduction of human dermal fibroblasts", Biomaterials, 1996 (17):1819-1825.*
Ehrmann, et al., "The Growth of Cells on a Transparent Gel of Reconstituted Rat-Tail Collagen," Journal of the National Cancer Institute, vol. 16, No. 6, 1375-1403, Jun. 1956.
Finkemeier, C.G. Bone-Grafting and Bone-Graft Substitutes Journal of Bone and Joint Surgery, vol. 84-A (3), Mar. 2002, pp. 454-464.

* cited by examiner

*Primary Examiner*—Ruth A Davis
(74) *Attorney, Agent, or Firm*—Morgan, Lewis & Bockius LLP

(57) ABSTRACT

The present invention is directed to a method of growing new bone, bone-like tissue or extracellular matrix under in vitro cell culture conditions. The method utilizes a bioreactor allowing for the flow of nutrient solutions into, through, and out of the bioreactor, wherein ground demineralized bone and bone-forming cells are present in the bioreactor. The resulting bone, bone-like tissue or extracellular matrix produced by the invention are within the scope of the present invention. In addition, the present invention is directed to the bioreactor device used to grow the new bone, bone-like tissue, or extracellular matrix.

30 Claims, 15 Drawing Sheets

(Imagine this in the shape of a jaw bone, big toe bone, finger bones, etc.)

Formed "Bone Plug"

7A  7B

8A

8B

8C

8D

New Collagen Production in Bioreactor

14A

New Collagen Production in Nude Mouse

14B

IN VITRO GROWTH OF TISSUES SUITABLE TO THE FORMATION OF BONE AND BONE FORMING TISSUE FORMED THEREBY

CROSS-REFERENCE TO RELATED APPLICATIONS

This application claims the benefit of U.S. Provisional Application Ser. No. 60/466,772 filed May 1, 2003, expressly incorporated herein by reference.

FIELD OF THE INVENTION

This invention relates to the formation of a tissue-engineered material using in vitro cell culture, in a bioreactor system(s), in the presence of biomaterials suitable for the induction of new bone formation. This invention further relates to the use of specific forms of reactors to cause the formation of a shaped material suitable to specific clinical applications. For example, the formation of a mandible-shaped reactor for in vitro growth of a shaped bone graft substitute for the use in repair of fractured jaws is within the scope of the present invention. This invention further relates to a bone forming tissue that will remodel into load-bearing bone when implanted in the surgical repair of bone defects.

BACKGROUND OF THE INVENTION

Demineralized bone matrix (DBM) is widely used in the repair of pathologies associated with skeletal defects and periodontal diseases. This material is typically produced from cortical bone of long-bones (chiefly those bones found in the legs and arms of human cadaveric donors) by cutting the shafts of these long-bones into small chunks (1-4 mm) using methods well-known in the field. The resulting pieces and chunks of bone are subsequently cleaned and grinded into a finer bone powder. The resulting bone powder is typically in the about 125 to 1000 micron particle size ranges. The bone powder may be demineralized by exposure to dilute (normally 0.4 to 0.6 N) hydrochloric acid, organic acids, calcium chelating agents, etc. as is known in the art. For example, U.S. Pat. Nos. 5,275,954; 5,531,791; 5,556,379; 5,797,871; 5,820,581; 6,189,537; and 6,305,379 describe methods of demineralizing bone material and are hereby incorporated by reference in their entirety. This ground demineralized bone matrix material has been called demineralized freeze-dried bone allograft (DFDBA), demineralized bone allograft (DBA), demineralized bone matrix (DBM), and demineralized bone (DMB) and is currently produced by a number of for profit and not-for-profit companies for use in orthopaedic, spinal fusion, and periodontal applications.

The use of DBM in the formation of new bone has been assessed using in vivo (usually a mouse or rat implant system), in vitro (cell culture or extraction and quantitation of bone forming molecules reportedly present in bone), and in situ (where the formation of new bone in patients has been assessed during clinical applications) applications. Methods of assessing this new bone formation and the effects of the demineralization process on new bone formation by DBM are described in Zhang et al., "A quantitative assessment of osteoinductivity of human demineralized bone matrix," *J. Periodontol.* 68:1076-1084 (1997) and Zhang et al., "Effects of the demineralization process on the osteoinductivity of demineralized bone matrix," *J. Periodontol.* 68:1085-1092 (1997). An in vitro assessment of the ability of DBM to induce cells towards an osteoblastic phenotype has also been described (Wolfinbarger and Zheng, "An in vitro bioassay to assess biological activity in demineralized bone," *In Vitro Cell Bio. Anim.* 29A:914-916(1993)).

DBM is assumed to form new bone when implanted in animal models via an endochondral pathway. The implanted DBM is presumed to cause mesenchymal stem cells (typically undifferentiated fibroblasts) to migrate towards the implanted biomaterial(s). This induced chemotaxis results in cells infiltrating the implanted DBM biomaterial(s) where they are induced to undergo phenotypic changes from a fibroblastic cell phenotype to a chondrocyte phenotype and eventually to an osteoblast cell phenotype. These induced phenotypic changes have been reported to be due to the action(s) of one or more small molecular weight proteins falling in the TGF-$\beta$ family commonly referred to as bone morphogenetic proteins (BMPs). As the change in cell phenotypes occurs, the proliferative potential of the cells declines. For example, the population doubling times increases from approximately 12 hours to approximately 40 hours. As a result, the cells synthesize and secrete collagens and other matrix-forming proteins/glycoproteins laying down a cartilagenous matrix and finally an osteoid-like matrix, which if left implanted in the animal long enough, can be shown to mineralize. This process is analogous to the formation of new bone. If the implanted materials lack the cell-inducing protein factors, only providing an environment suitable for cellular infiltration and cellular proliferation and differentiation, the implanted materials are deemed to be osteoconductive. If the implanted materials possess the cell inducing protein factors and provide an environment suitable for cellular infiltration and cellular proliferation and differentiation, the implanted materials are deemed to be osteoinductive. If the implanted materials already contain cells suitable for new bone formation, such as autogenously transplanted bone, the materials are deemed to be osteogenic.

SUMMARY OF THE INVENTION

The present invention is directed to a method of growing new bone or bone-like tissue under in vitro cell culture conditions comprising providing ground demineralized bone and bone-forming cells in a bioreactor under conditions sufficient to form bone or bone-like tissue suitable for transplantation by causing a flow of nutrient solutions into, through, and out of the bioreactor. The bone or bone-like tissue is formed by proliferation and/or differentiation of the bone-forming cells in the presence of the ground demineralized bone and under suitable bioreactor conditions.

The bone-forming cells are preferably selected from the group consisting of stem cells, fibroblast cells, periosteal cells, chondrocytes, osteocytes, pre-osteoblasts, and osteoblasts. The most preferred bone-forming cells are fibroblast cells and pre-osteoblasts. The bone-forming cells can be autogenic, allogenic or xenogenic with respect to the intended recipient.

In accordance with the invention, the ground demineralized bone may be in the form of particles or fibers. The particles are about 50 microns to about 4 mm, preferably about 250 microns to about 710 microns. The fibers have a width of about 0.1 mm to about 0.5 mm, a thickness of about 0.05 mm to about 0.5 mm, and a length of about 1 mm to about 500 mm. If the ground demineralized bone is freeze-dried, it should be rehydrated. The invention provides that rehydration may occur either prior to or after being added in the bioreactor.

The invention further provides that additional components may be added to the bioreactor, such as collagen or hyaluronin, which may create a viscous bone-like matrix. Additionally, growth factors, such as vascular endothelial growth factor or differentiation factors such as bone morphogenetic proteins may be added.

The nutrient solution may comprise at least one of Dulbecco's modified Eagle's medium, fetal bovine serum, L-ascorbic acid-2-phosphate, antibiotics, dexamethasone, beta-glycerolphosphate, glucose, glutamine, amino acid supplements, glutathione-ethyl ester, antioxidants, caspase inhibitors, and inorganic ions suitable for mineralization-related metabolic events.

The nutrients solution may be delivered to the ground demineralized bone and bone-forming cells by resorbable hollow fibers. The hollow fibers are also sufficient to remove metabolic waste products from the bioreactor.

In another aspect of the invention, nondemineralized bone may be added along with the demineralized ground bone. The ratio of demineralized ground bone to nondemineralized bone may be about 1:1 to about 20:1 or as necessary to control availability of biologically active agents and available volume for cell growth.

The present invention is further directed to the bone or bone-like tissue formed according to the process disclosed herein. Moreover, implants comprising the bone or bone-like tissue is within the scope of the invention.

Furthermore, a method for growing an extracellular matrix capable of forming bone when transplanted into a patient is described. The method comprises providing bone-forming cells in a bioreactor under conditions sufficient to promote the growth and differentiation of cells resulting in the formation of an extracellular matrix, wherein said conditions include the flow of nutrient solutions through the bioreactor. Preferably, ground demineralized bone is added to the bioreactor. The present invention further encompasses the extracellular matrix made by this process and a method of implanting bone into a patient in need thereof comprising transplanting the formed extracellular matrix into the patient under conditions sufficient to form bone.

In yet another aspect of the invention, a device for the growth of new bone or bone-like tissue under in vitro cell culture conditions is provided. The device comprises a bioreactor, wherein the bioreactor comprises inlet and outlet ports for the flow of nutrient solutions, sample injection ports, and an inlet port and outlet port for the bioreactor to cyclically receive negative pressure and positive pressure. The bioreactor may optionally include hollow fibers for the delivery of nutrients and removal of wastes. The bioreactor is capable of applying mechanical/electrical stimuli to the formed or forming bone.

The bioreactor may further comprise an outer nondeformable chamber and inner deformable chamber. Either of these chambers may receive or remove the nutrient solutions via the inlet and outlet ports. In addition, the sample injection port may contact either chamber in which the bioreactor will receive biomaterials. Additional ports may be available to allow the bioreactor to receive cyclical negative and positive pressure in the volume between the outer nondeformable chamber and the inner deformable chamber through the inlet and outlet ports. Endplates may be used to secure the bioreactor and provide apertures to receive the ports.

Preferably, the device comprises hollow fibers, which can be in any shape. The hollow fibers can be round and tubular, or in the form of concentric rings. The hollow fibers may be made of a resorbable or non-resorbable membrane comprising polydioxanone, polylactide, polyglactin, polyglycolic acid, polylactic acid, polyglycolic acid/trimethylene carbonate, cellulose, methylcellulose, cellulosic polymers, cellulose ester, regenerated cellulose, pluronic, collagen, elastin, or combinations thereof. The pores of hollow fibers are of a specified diameter that extend from the inside to the outside of the wall of the hollow fiber. For example, the pores may have a diameter of about 2 kiloDaltons to about 50 kiloDaltons, preferably about 5 kiloDaltons to about 25 kiloDaltons, or alternatively, about 2 kiloDaltons to about 15 kiloDaltons.

In accordance with the present invention, the device may include an inner deformable chamber comprising a deformable wall. The deformable comprising a flexible permeable barrier. The flexible permeable barrier may comprise a resorbable or non-resorbable membrane made up of polydioxanone, polylactide, polyglactin, polyglycolic acid, polylactic acid, polyglycolic acid/trimethylene carbonate, cellulose, methylcellulose, cellulosic polymers, cellulose ester, regenerated cellulose, pluronic, collagen, elastin, or a combination thereof. In addition, the inner deformable chamber may further comprises a fine mesh. Preferably, the fine mesh comprises sterilizable materials and is made up of stainless steel, titanium, plastic polymer, nylon polymer, braided collagen, silk polymer, or a combination thereof. The fine mesh may have any suitable pore size range such as, for example, between about 0.1 to about 10 mm, about 1 mm and about 5 mm. The fine mesh may be on the inner surface of the flexible permeable barrier, outer surface or both.

Figure 11:
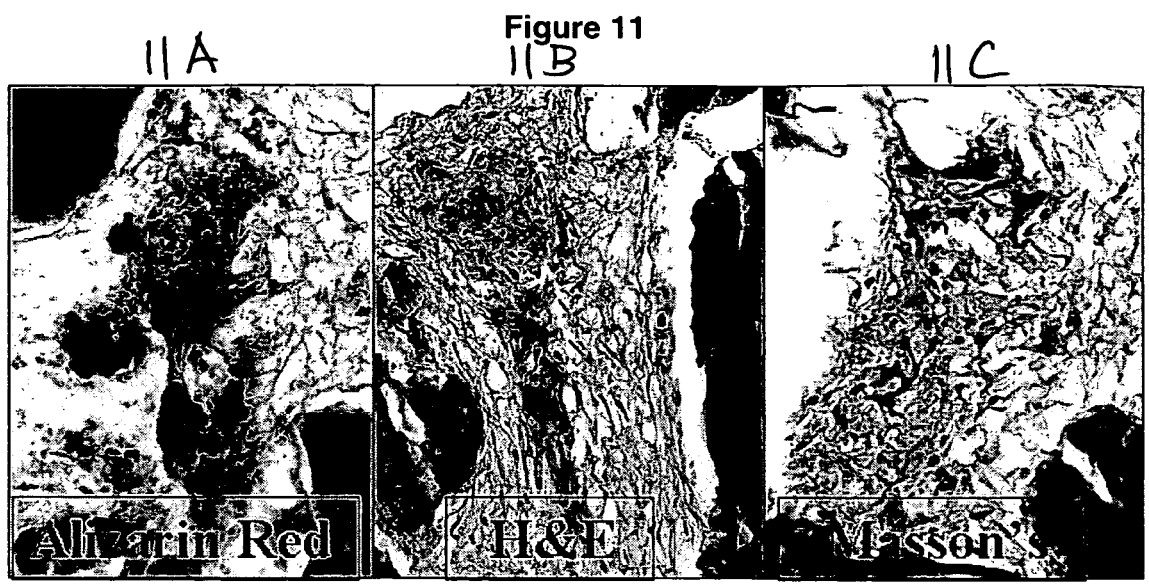
FIGS. 11A, B, and C illustrate the histological analysis of a "bone plug" generated in a bioreactor according to the method of the present invention at 200× magnification. The "bone plug" generated in bioreactor was embedded and sectioned. The sections were stained with the Alizarin Red (FIG.

11A), H&E (FIG. 11B), and Masson's Trichrome (FIG. 11C) methods. The Alizarin Red staining revealed the calcium deposition in newly formed extracellular matrix. H&E staining revealed the changes in fibroblast morphology and new extra-cellular matrix (ECM) production that appeared to be "osteoid" formation. Masson's Trichrome staining suggested that the newly formed extracellular matrix contained significant quantities of collagen.

Figure 12:

FIG. 12 illustrates the histological analysis of a "bone plug" generated in a bioreactor according to the method of the present invention at 400× magnification. The sections were stained with the Alizarin Red (FIG. 12A), H&E (FIG. 12B), and Masson's Trichrome (FIG. 12C) methods. The Alizarin Red staining revealed the calcium deposition in newly formed extracellular matrix. H&E staining revealed the changes in fibroblast morphology and new extra-cellular matrix (ECM) production that appeared to be "osteoid" formation. Masson's Trichrome staining suggested that the newly formed extracellular matrix contained significant quantities of collagen.

Figure 13:
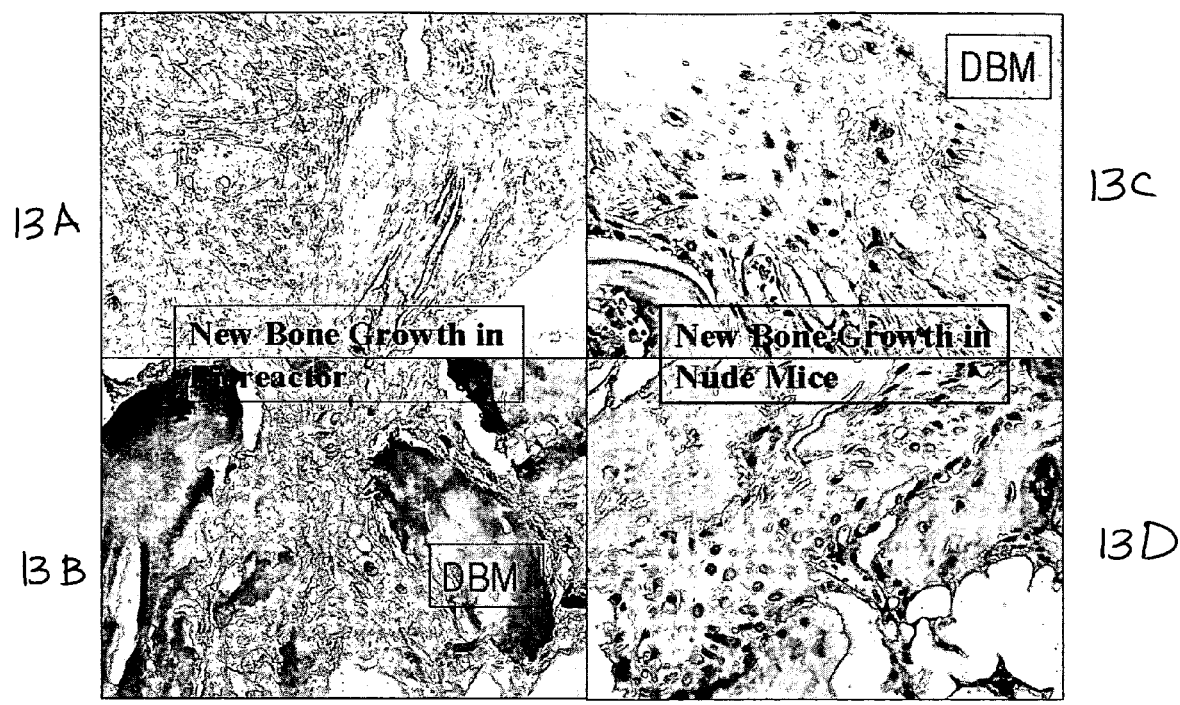

FIGS. 13A-13B illustrate the H&E staining of a "bone plug" generated in a bioreactor according to the method of the present invention and FIGS. 13C-13D illustrate the H&E staining of an analogous "bone plug" generated from heterotopic implantation of DBM in a nude mouse (400× magnification). The new bone growth in a bioreactor after 4 weeks incubation was compared to the new bone growth in a nude mouse 4 weeks after DBM implantation. The changes in fibroblast morphology and new extracellular matrix production appeared on samples.

Figure 14:

FIG. 14A illustrates the Mason's Trichrome staining of a "bone plug" generated in a bioreactor according to the method of the present invention and FIG. 14B illustrates an analogous "bone plug" generated from heterotopic implantation of DBM in a nude mouse (400× magnification). Significant amounts of new extracellular matrix were produced around cells and stained as collagen fibril for both "bone plug" generated in a bioreactor and explants from a nude mouse.

Figure 15:
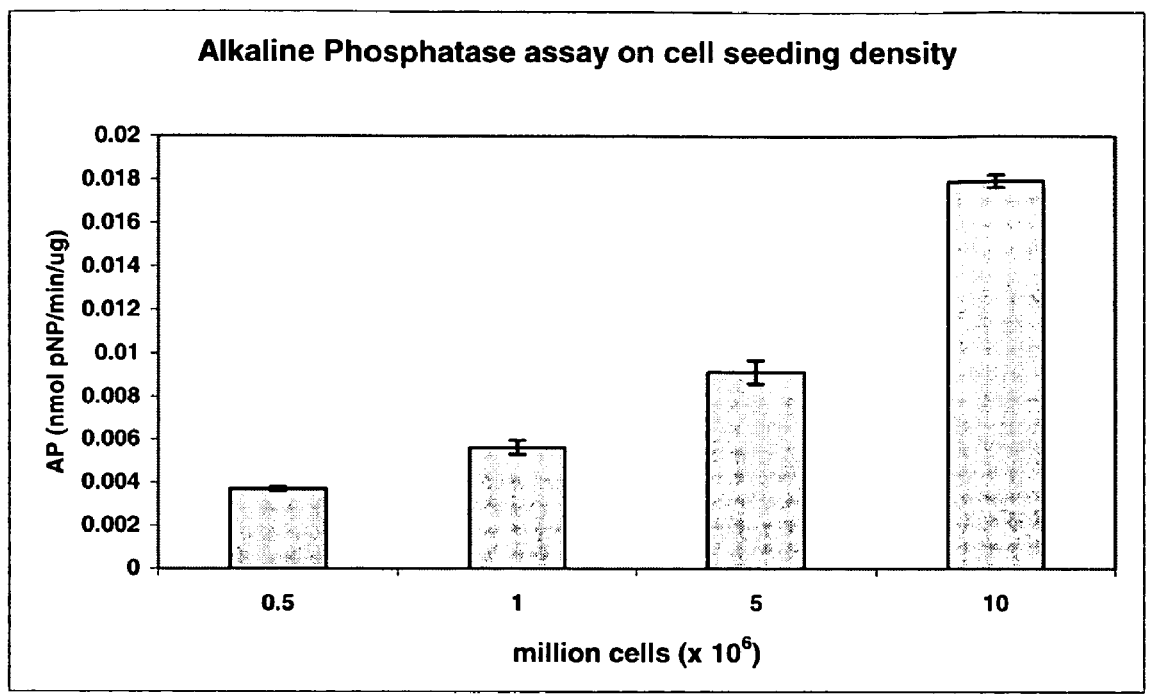

FIG. 15 depicts a graph of the alkaline phosphatase (nmol pNP/min/µg) activity for "bone plugs" generated in a hollow fiber bioreactor with various cell seeding densities (0.5, 1, 5, and 10 millions human periosteal cells per 500 mg of DBM).

FIGS. 16A and 16B illustrate the H&E staining for a "bone plug" generated in a hollow fiber bioreactor (400× magnification) according to the method of the present invention.

DESCRIPTION OF THE PREFERRED EMBODIMENTS

It must be noted that as used herein and in the appended claims, the singular forms "a", "and", and "the" include plural references unless the context clearly dictates otherwise. Thus, for example, reference to "a nutrient solution" includes a plurality of such solutions and reference to "the vessel" includes reference to one or more vessels and equivalents thereof known to those skilled in the art, and so forth.

Unless defined otherwise, all technical and scientific terms used herein have the same meaning as commonly understood to one of ordinary skill in the art to which this invention belongs. Although any methods, devices, or constructs similar or equivalent to those described herein can be used in the practice or testing of the invention, the preferred methods, devices, or constructs are now described.

The term "bioreactor" is intended to mean a contained or enclosed system or vessel for the culture of cells, such as mammalian or vertebrate cells, by which sterility or the freedom from microbial contamination can be achieved. Nutrient solutions can be aseptically delivered into the bioreactor and waste solutions can be aseptically removed from the bioreactor.

The term "newly formed bone" is intended to mean a matrix secreted by bone-forming cells. This newly formed bone is best illustrated by histological evidence of newly formed bone when demineralized bone is implanted intermuscularly in a nude mouse (or rat) bioassay system. For example, FIG. 12 depicts new bone growth in a bioreactor within the scope of the present invention.

The term "bone tissue" is intended to include the organic phase or organic and inorganic phases of that tissue comprising a bone. Within the context of this invention, bone tissue can include newly formed bone, implant bone, and associated cells, bone marrow, bone marrow-like tissue, and cartilage (and cartilage-like tissues).

The term "bone-like tissue" is intended to include a matrix similar to cartilage and/or osteoid similar to that tissue found in articular cartilage, mineralized adult bone, nonmineralized fetal bone, or tissues consisting primarily of type 1, type 2 collagens, hyaluronic acid (hyluronans), proteoglycans, and non-collagenous proteins similar to those proteins found in bone and/or cartilagenous tissues. This matrix will be suitable for the growth and differentiation of chondrocytes, chondrocyte-like cells, osteocytes, osteoblasts, and/or osteoblast-like cells.

The term "transplantable bone" is intended to include a nonmineralized, partially mineralized, or fully mineralized viable construct produced, using a bioreactor, that is nonload-bearing, partially load-bearing, or fully load-bearing at the time of transplantation.

The term "implantable bone" is intended to include a nonmineralized, partially mineralized, or fully mineralized nonviable acellularized construct produced, using a bioreactor, that is nonload-bearing, partially load-bearing, or fully load-bearing at the time of implantation.

The term "strain" is intended to include forces applied to the cells and matrix contained in a bioreactor that contribute to manipulation of phenotype of the cells contained therein. As used in the present invention, strain is expected to be applied to the cells and matrix in the bioreactor through forces applied to and within the bioreactor.

The term "stress" is intended to include forces applied to the cells and matrix contained in a bioreactor that contribute to manipulation of phenotype of the cells contained therein. As used in the present invention, stress is expected to be applied to the cells and matrix in the bioreactor through forces applied to and within the bioreactor.

The term "hollow fiber" is intended to include tubular structures containing pores of defined size, shape and density for use in delivering nutrients (in solution) to cells contained within a bioreactor and for removal of waste materials (in solution) from cells contained within a bioreactor. For purposes of the present invention, hollow fibers may be constructed of a resorbable or nonresorbable material.

The term "nutrient solution" is intended to include solutions entering a bioreactor and containing those nutrient materials essential to the culture of mammalian or vertebrate cells. Nutrient solutions may also contain additives that affect specific changes in phenotype of cells under culture or to contribute to changes in the matrix structure of the forming newly formed bone, such as, mineralization.

The term "waste solution" is intended to include solutions exiting a bioreactor and containing waste byproducts of cellular metabolism. The concentrations of waste byproducts, for example ammonia, lactic acid, etc. and residual levels of nutrients such as glucose, in the waste solution can be used to assess the levels of metabolic activity of cells being cultured in a bioreactor.

The present invention provides a method of growing bone in vitro involving providing a biomaterial, such as ground demineralized bone, suitable for inducing cells to form an extracellular matrix and cells capable of forming bone or bone-like biomaterials, and placing the biomaterial and bone-forming cells in close association under conditions suitable for forming bone or bone-like biomaterial. In particular, the ground demineralized bone and bone-forming cells are preferably placed in a bioreactor capable of simulating the nutrient flow and waste removal present within an implant site. The flow of nutrient solutions into, through, and out of the bioreactor permit the associated ground demineralized bone and bone-forming cells to form into bone or bone-like biomaterial suitable for transplantation.

The biomaterial, ground demineralized bone, is capable of inducing selected cell types to form an extracellular matrix consistent with the osteoid materials comprising the organic phase of bone tissue when implanted in heterotopic or orthotopic sites in a living organism. Ground demineralized bone is obtained in manners known in the art and may be available in any form, including as particles or fibers. Ground demineralized freeze-dried bone particles may be used in any particle size suitable for inducing the growth of bone in a bioreactor, such as from about 50 microns to 4 mm, preferably, about 125 microns to 850 microns, and most preferably, about 250 microns to 710 microns. Ground demineralized bone fibers may be produced in known manners, such as by skiving or shaving the surface of the cortical bone to produce short fibers that easily entangle. The fibers are suitable for growing bone in a bioreactor and preferably have physical dimensions of about 0.1 mm to 0.5 mm in width, 0.05 mm to 0.5 mm in thickness, and 1 mm to 500 mm in length. The bone used to make the ground demineralized bone may be processed in known manners prior to forming the ground demineralized bone used in connection with the present invention. For example, the bone may be treated with enzymes to partially digest the organic components of the bone, such as collagenase, papain, protease, hyaluronidase, endonuclease, lipase, and/or phosphatase, or organic acids, such as acetic or citric acid. Alternatively, the bone may be partially digested by fragmenting the covalent bonds in the individual collagen molecules contained in the demineralized bone. The covalent bond breakage of the formed fragments of a collagen molecule may be in the range of about 2 to about 50, and should be sufficient to modify the resorption rate of the demineralized bone. Subsequent to forming the fibers or particles, the fibers and particles are demineralized by exposure to dilute (about 0.4 to 0.6 N) hydrochloric acid or organic acids, calcium chelating agents, etc., as one skilled in the art would appreciate. Alternatively, non-acid chelators of calcium, such as ethylene diamine tetraacetic acid (EDTA), may be used to demineralize the bone.

In addition, the weight percent residual calcium in ground demineralized bone is a factor in defining the bioavailability of bioactive molecules, such as, for example, bone morphogenetic proteins (BMPs), to the cellular population contained within the bioreactor. In fact, it has been found that the ability to extract BMPs from ground bone particles has been shown to be approximately a linear function of the extent of demineralization of the ground bone. Thus, a suitable amount of residual calcium is that amount sufficient to optimize the bioavailability of bioactive molecules, such as BMPs, to the bone-forming cells in the bioreactor. Preferably, the residual calcium is present in the range of about 0-8 weight percent, more preferably about 1-4 weight percent, and most preferably about 2 weight percent.

In accordance with the present invention, the ground demineralized freeze-dried bone particles are added aseptically to the bioreactor. They may be directly added to the bioreactor in a freeze-dried state and rehydrated in the bioreactor or rehydrated in culture medium prior to addition to the culture chamber of the bioreactor. The ground demineralized bone may be added alone or in combination with other components. Preferably, the other components do not inhibit the effect of the ground demineralized bone to induce bone formation. For example, ground nondemineralized bone may be added with ground demineralized bone. In such cases, the ground demineralized bone to nondemineralized bone may be added in any ratio, but preferably is added in a ratio of about 1:1 to about 20:1, more preferably about 8:1, and most preferably about 3:1. The ground nondemineralized bone may take any form, e.g., particles or fibers, and typically will have similar physical dimensions as the ground demineralized bone.

Particle size ranges of the ground demineralized bone particles in the bioreactor determine the "void volume" or available volume outside of the ground demineralized bone particles in which the bone-forming cells and other components may be added. It has been found that the bone particle spacing or availability of space around the ground demineralized bone particles within the bioreactor relates to the void volume and has an impact on the ability of bone-forming cells in the bioreactor to differentiate and/or proliferate. It is desired that bone-forming cells have sufficient contact to allow those cells to infiltrate the voids or space between the ground demineralized bone particles, which permits the in vitro growth of bone or bone-like tissue. Therefore, the void volume or spacing around the ground demineralized bone particles should be that which is effective in allowing for the optimal contacting and infiltration of voids by bone-forming cells between the ground demineralized bone particles.

In accordance with the present invention, the ground demineralized bone particles may be rehydrated in the bioreactor or prior to being added to the bioreactor. Preferably, the particles are rehydrated and mixed with bone-forming cells prior to addition to the bioreactor. The ground demineralized bone particle spacing will differ depending on whether or not the bone particles are rehydrated prior to addition to the bioreactor growth chamber. First, the ground demineralized bone particles may be added to the bioreactor growth chamber and subsequently rehydrated prior to adding bone-forming cells. In this approach, the ground demineralized bone particles may be added to the bioreactor growth chamber in a freeze-dried state, which provides a relatively simple step and allows the particles to pack tightly filling the available space. Subsequent rehydration of these freeze-dried ground demineralized bone particles in the bioreactor will cause the bone particles to swell to a tighter state of packing due to rehydration. The bone-forming cells may then be added to the rehydrated bone matrix void volume (that volume outside of the bone particles) in the bioreactor. It has been found this tighter state of packing ground demineralized bone particles in the bioreactor is effective in more tightly packing the added bone-forming cells. While the tight packing may hinder some infiltration of the void volume present throughout the bioreactor, it has been found that the more tightly packed added cells promotes better retention of synthesized matrix molecules during the differentiation process and may be best utilized when seeding more differentiated cells into the bioreactor system.

Alternatively, the ground demineralized bone particles may be rehydrated prior to the addition to the growth chamber of the bioreactor. The bone-forming cells may then be added to the packed ground demineralized bone particles in the bioreactor or directly to the rehydrated bone particle suspension prior to its addition to the bioreactor. While rehydrating freeze-dried ground demineralized bone particles prior to addition to the growth chamber of the bioreactor has been found to increase the difficulty in adding the bone particles to the bioreactor, it has been found that directly adding the bone-forming cells to the rehydrated ground demineralized bone particle suspension results in fully dispersed bone-forming cells and ground demineralized bone particles. More uniform distribution within the growth chamber is thereby achieved and is less likely to contribute to damage to the hollow fibers present within the growth chamber.

In either case, centrifugal forces can be used to cause the rehydrated bone particles and cells to pack throughout the growth chamber with excess fluids removed from the packing port.

The "bone-forming cells" of the present invention are those cells suitable for the induction of new bone formation when infiltrated with ground demineralized bone in a bioreactor and include those cell types suitable for differentiating into bone cells or suitable for forming a matrix similar to osteoid of forming new bone. Suitable cell types include, but are not limited to stem cells, fibroblast cells, periosteal cells, chondrocytes, osteocytes, pre-osteoblasts, and osteoblasts. Preferably, the stem cells are multipotent, the fibroblast cells are undifferentiated, the periosteal cells are partially differentiated, and the chondrocytes or osteocytes are differentiated. In the case of differentiating cell types, such as fibroblasts or stem cells, these cell types may be placed in close proximity to the ground demineralized bone, which, in the bioreactor and under appropriate conditions, will cause the cells to differentiate into bone cells. In the case of cell types suitable for forming an osteoid-like matrix, such as osteoblasts or chondroblasts, such cell types may be placed in close proximity to the ground demineralized bone in the bioreactor and under appropriate conditions, will cause the cells to synthesize matrix similar to osteoid of forming new bone. The type of cells selected for in vitro bone growth is dependent upon the desired time frame for new bone formation, seeding cell densities, and nutrient medium provided.

The source of the bone-forming cells may be autogenic, allogenic, or xenogenic. The use of a potential recipient's own cells in the formation of the bone or bone-like biomaterial will result in a tissue unlikely to be rejected for some immunological reason, rendering the transplantable newly formed bone autogenous in nature. The use of allogenic cells in the formation of new bone with subsequent implantation can be achieved by decellularizing any newly formed bone or bone-like structure prior to implantation using any decellularizing technology known in the art depending on the desired characteristics of the acellular bone or bone-like structure desired for a given clinical application.

The bone-forming cells are added either to the void volume space of the packed ground demineralized bone particles or directly to the rehydrated ground demineralized bone particles prior to addition to the growth chamber of the bioreactor. The cell density of the bone-forming cells may be in the range of from about $10^2$-$10^8$ cells per ml, preferably $10^3$-$10^6$ cells per ml, and more preferably about $10^4$-$10^5$ cells per ml. The density of bone-forming cells added depends on several factors. For example, previous cell culture work in development and validation of in vitro bioassays for assessing the osteoinductive potential of demineralized bone demonstrated the importance of cell density difference depending on the phenotypic status of the cells. (Wolfinbarger, L and Y. Zheng. 1993. An in vitro bioassay to assess biological activity of demineralized bone. In Vitro Cell Dev. Biol. Anim. 29:914.) Less differentiated cells (e.g., dermal fibroblasts), where proliferation constituted a component of the differentiation process, involved a lower seeding density in in vitro bioassays than more differentiated (periosteum derived cells, for example) cells. Presumably, cells more differentiated along the pathway leading from a "stem-like" cell to a differentiated cell phenotype proliferated less well (longer population doubling times of approximately 40 hours) than less differentiated cells (shorter population doubling times of approximately 12 hours) and could be seeded at higher cell densities when used in an in vitro bioassay. Consequently, seeding densities of cells in the bioreactor depends in part on the phenotype of the cells added to the bioreactor, the availability of biologically active materials, and the culture medium used. In addition, seeding cell density in the bioreactor depends on the ability to deliver nutrients to the cells and remove waste byproducts from the bioreactor culture chamber. For example, greater cell densities in the bioreactor require more nutrient delivery and greater waste product removal than lower cell densities.

The bioreactor can be in virtually any shape based on the shape of the bioimplant desired as a newly formed bone or structure that will form load-bearing bone when implanted clinically. The wall of the bioreactor can be deformable and contained within a nondeformable chamber such that positive and negative pressure environments can be applied between the inner wall of the nondeformable chamber and the outer wall of the deformable chamber such that the volume of the bioreactor containing the demineralized bone, cells, and matrix can be decreased or increased over time to simulate stress and strain application to the bone matrix being formed.

The demineralized bone and bone-forming cells can be preloaded into the bioreactor in the presence, or lack thereof, of a viscous matrix designed to provide attachment sites for the cells and/or to restrict diffusion of synthesized osteoid forming molecules. The viscous nature of the matrix may be obtained by the incorporation of polymers, for example, collagenous, hyaluronin, or similar resorbable or nonresorbable polymers.

Nutrients are delivered to the ground demineralized bone and bone-forming cells in the bioreactor and may impact the growth and differentiation of cells contained in the bioreactor. The nutrient solutions are selected to provide sufficient nutrition to the bone-forming cells to maintain viability, growth, and/or differentiation in the bioreactor. Those skilled in the art are capable of selecting an appropriate nutrient solution for the present invention. For example, media such as Dulbecco's modified Eagle's medium may be used and may be further supplemented with other suitable nutrients. Other suitable nutrients include fetal bovine serum, L-ascorbic acid,-2-phosphate, antibiotics, cell modulators such as dexamethasone, beta-glycerolphosphate, glucose, glutamine, amino acid supplements, inhibitors (or activators) of apoptosis such as glutathione-ethyl ester, antioxidants, caspase inhibitors, and cations and anions, e.g., magnesium, manganese, calcium, phosphate, chloride, sodium, potassium, zinc, and sulfate ions, and nitrates and nitrites. The concentration of fetal calf serum must not inhibit induced cell differentiations due to diffusible agents from the demineralized bone. The remaining concentration of components in the nutrient solution should be sufficient to promote growth and/or differentiation in the bioreactor and maintain viability of the bone-forming cells and the resulting bone or bone tissue.

In accordance with the present invention, the nutrient solutions may be modified during different phases of the process. For example, during initial culture, seeded cell densities may be minimal, especially for fibroblast cell seeding cultures, and thus nutrient solutions may contain low concentrations of fetal calf serum (such as ≦2% vol:vol) to facilitate the role of growth and differentiation factors diffusing from the ground demineralized bone particles in modulating phenotypic changes in the added cells. Monitoring the concentration of the nutrients, such as glucose, glutamine, and amino acid supplements, via the eluent flow of medium allows for the determination of nutrient consumption permitting control of flow (delivery) of nutrients into the cell population. Moreover, waste products of metabolism, for example, ammonia and lactic acid, can be monitored via the eluent flow of medium from the bioreactor to determine the metabolic state/function of the resident cell population. Changes in cell phenotype during the culture phase can be monitored by sampling the eluent flow of medium from the bioreactor for proteins associated with specific cell phenotypes, for example, osteopontin and osteocalcin. Should it be desired, for example, other components may be added to the medium during culture to promote a desired function. For example, to induce mineralization during a specific phase of the culture period, chemical components such as β-glycerolphosphate may be added to the medium as a substrate for alkaline phosphatase and to serve as a source of phosphate to be complexed with calcium in the formation of crystalizable calcium salts such as hydroxyapatite. Alternatively, hormonal stimulation of cells can be accomplished via the addition of certain compounds such as, for example, vitamin D. The levels of oxygen tension can be controlled by oxygenation of the nutrient medium being added to the cells being cultured in the bioreactor to manipulate the metabolic state of the cells during the culture phase such that mildly hypoxic conditions can be used to manipulate chondrogenesis and/or osteogenesis. Manipulation of the ionic composition of the medium can be used to control hydrolytic enzyme degradation of demineralized bone matrix, enzyme mediated cross-linking of the formed extracellular matrix being synthesized by the resident cell population, and the osmotic balance of the nutrient solution. Induction and/or inhibition of cellular apoptosis can be controlled by the addition of inhibitors (or activators) of apoptosis such as glutathione-ethyl ester, antioxidants, and caspase inhibitors or activators. For example, use of allogenic cells may require induction of apoptosis to produce acellular formed bone tissue. In addition, gamma irradiation treatment of the bone particles, either before or after demineralization, can be used to promote cell-mediated resorption of the demineralization bone particles facilitating new bone formation within the areas where the bone particles are resorbed.

The nutrients may be delivered in any manner suitable for the formation of bone in the bioreactor. For example, resorbable hollow fibers can be used to deliver nutrients and remove metabolic waste products during the cellular proliferations and/or differentiation process. The nutrient solutions used can be sequentially introduced into the bioreactor growth chamber as needed to induce cellular morphogenesis, growth, secretion of osteoid biomaterials, and/or to cause mineralization of the formed matrix as desired depending on the type of implantable bone material desired. The resorbable hollow-fibers used to deliver nutrients and remove wastes from the bone forming part of the bioreactor provide an opportunity to leave a series of hollow tube-like openings within the formed bone tissue through which the formed bone tissue can be vascularized. Growth factors such as vascular endothelial growth factor (VEGF) can be final delivered through these hollow fibers once the bone tissue has been formed to promote angiogenesis within the hollow structures following transplantation.

Delivery of nutrients and removal of waste products depends primarily on two factors: numbers of hollow fibers per unit volume of the culture chamber of the bioreactor and flow rates of nutrient solutions through the hollow fibers.

The hollow fibers of the present invention are those suitable for the delivery of nutrients and removal of waste in the bioreactor. The hollow fibers may be any shape, for example, they may be round and tubular or in the form of concentric rings. The hollow fibers may be made up of a resorbable or non-resorbable membrane. For example, suitable components of the hollow fibers include polydioxanone, polylactide, polyglactin, polyglycolic acid, polylactic acid, polyglycolic acid/trimethylene carbonate, cellulose, methylcellulose, cellulosic polymers, cellulose ester, regenerated cellulose, pluronic, collagen, elastin, and mixtures thereof. Moreover, the hollow fibers of the present invention include pores to allow the nutrients and waste to pass in and out of it. The pores of the hollow fibers are a sufficient diameter to allow the diffusion of a molecule from one side of the hollow fiber to the other side of the hollow fiber. Preferably, the molecules that may pass through the hollow fiber pores are about 0.002 to about 50 kDa, more preferably about 5-25 kDa, or most preferably 2-15 kDa.

Figure 4:
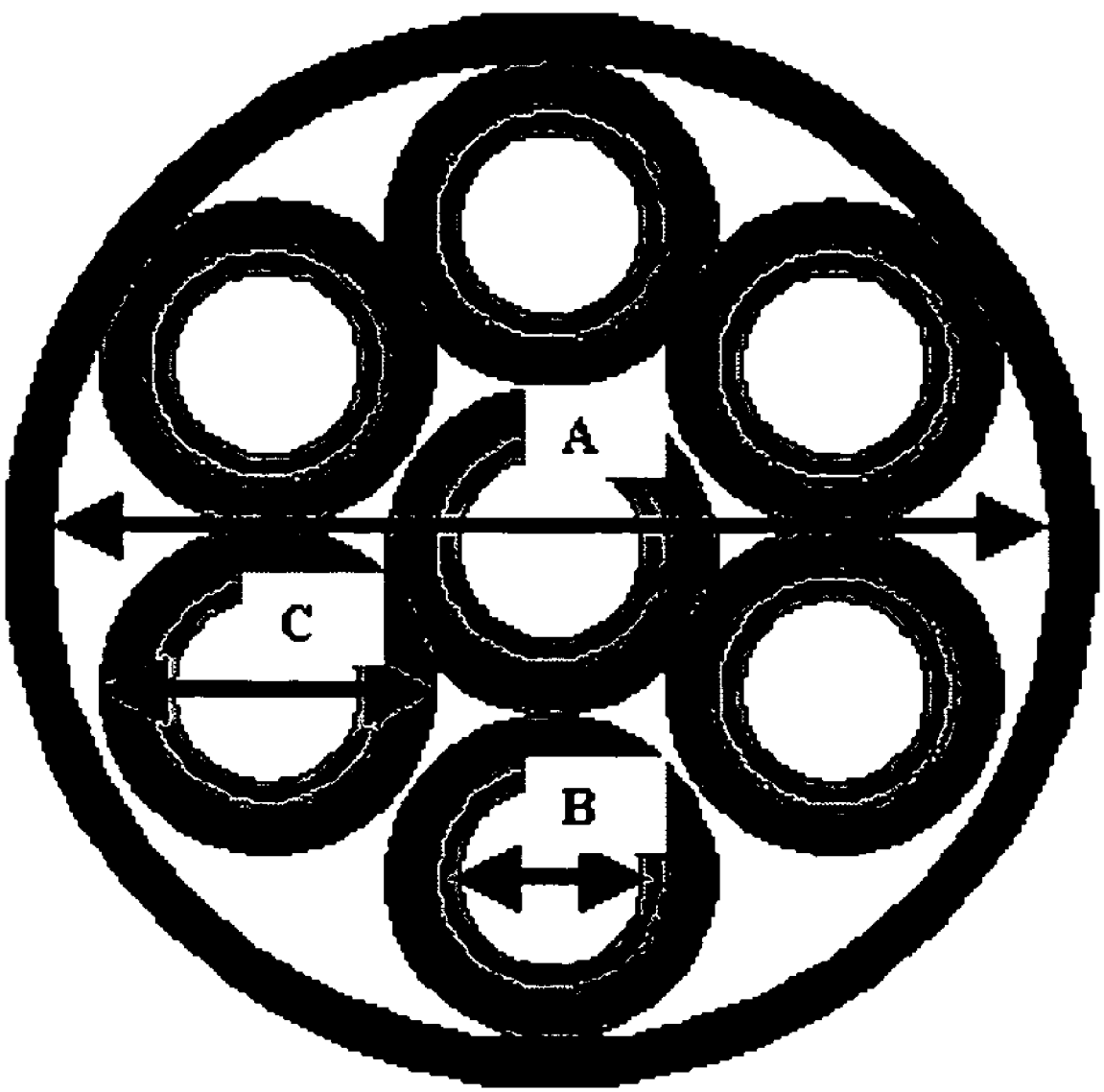
FIG. 4 depicts a cross section of a hollow fiber bioreactor within the scope of the present invention, which assists in the calculation of the number of hollow fibers for one bioreactor.

The number of hollow fibers per unit volume of the culture chamber of the bioreactor is determined based on the cross-section of the hollow fibers, the bioreactor per se, and the distance the bone-forming cells can live from the hollow fibers for nutrient delivery and waste removal. As an example of determining the number of hollow fibers per unit volume, FIG. 4 illustrates the cross section of a hollow fiber bioreactor. Assume the bioreactor cross section inner diameter (ID) is 2 cm (A), one hollow fiber ID is 1 mm (B), and the distance of cells can live from any conduit for nutrient delivery and waste removal is 20 μm, the ID of the circular area where nutrient deliver and waste remove by one hollow fiber (C) should equal to B+20×2 μm. Thus the number of hollow fibers needed for bioreactor can be calculated as follows:

1) Bioreactor ID (A)=2 cm
2) Hollow Fiber ID (B)=1 mm

Distance of Cells Can Live From Any Conduit for Nutrients Delivery and Waste Removal approximates 20~30 μm depending on the diffusion rates of the nutrient molecules. According to human physiology, it is rare that any single functional cell of the body is more than 20-30 μm away from a capillary.

3) Calculation:

Total Area of Cross-section of Bioreactor =

$$(A/2)^2 * \pi = (2cm/2)^2 * \pi = (10 \text{ mm})^2 * \pi = 100 \text{ mm}^2 * \pi$$

Total Area of Cross-section of One Hollow Fiber =

$$(B/2)^2 * \pi = (1 \text{ mm}/2)^2 * \pi = 0.25 \text{ mm}^2 * \pi$$

Total Area of Nutrients Delivery and Waste Removal of One Hollow Fiber=$(C/2)^2*\pi$=$(1 \text{ mm}/2+0.02 \text{ mm})^2*\pi$= $(0.5 \text{ mm}+0.02 \text{ mm})^2*\pi$=$0.2704 \text{ mm}^2*\pi$ Number of Hollow Fibers for Bioreactor with Cross-Section ID of 2 cm=100 mm$^2$* π/0.2704 mm$^2$*π=369.82≈370

Percentage of Total Area Covered by Hollow Fibers=(0.25 mm$^2$*π)*370/100 mm$^2$* π*100=92.6%

Percentage of Total Area Covered by Nutrients Delivery and Waste Removal=(0.2704 mm$^2$*π)*370/100 mm$^2$*π*100=100.48%

Although the flow of nutrient solutions through the hollow fibers will generate some minimal turbulent flow of solutions through the bulk volume of the growth chamber of the bioreactor, the primary mechanism for nutrient dispersal through the growth chamber and to the cells in culture will be diffusion and/or the alternating positive and negative pressure applications applied to the deformable bioreactor wall used to apply stress/strain to the demineralized bone, cells, and extracellular formed/forming matrix mixture during the culture process. Diffusion of nutrients from capillary beds in tissue typically limits the provision of nutrients (for example oxygen, glucose, etc.) to 20-30 μm from an individual capillary. Thus, if diffusion were the sole determinant of nutrient delivery and waste removal, it should be expected that cells located more than 20-30 μm from a hollow fiber will receive less nutrients and exist in a greater concentration of waste byproducts than cells close to a hollow fiber. With application of stress/strain to the demineralized bone, cells, and extracellular formed/forming matrix mixture via alternating applications of positive and negative pressure, it becomes possible to affect greater nutrient solution delivery and waste removal permitting cultivation of cells at greater distances from the hollow fibers than would be allowed by simple diffusion.

Shear stress to cells present in the bioreactor due to flow of nutrient solution will be minimal. Thus, optional addition of mechanical stress and strain to the forming bone matrix will occur primarily via manipulation of the inner vessel in the bioreactor used to contain the demineralized bone, cells, and extracellular formed/forming matrix. This component of the bioreactor includes the option of placing an inner vessel constructed of a deformable material within an outer vessel to which cyclic positive and negative pressure can be applied via a port in the outer vessel wall. It is to be expected that such positive and negative pressures will be minimal and designed to gently compress and expand the forming extracellular matrix in order to provide cyclic mechanical stimulation to the cells contained within the inner vessel of the bioreactor and to promote nutrient solution flow into, through, and out of the bioreactor containing the cells and matrix mixture.

In addition to the cyclic mechanical stimulation to cells contained within the inner vessel of the bioreactor, the inclusion of a series of micro-electrodes within the inner wall of the inner vessel in liquid contact with the forming, or formed, extracellular matrix will allow cyclic, low-level, electrical stimulation of cells and/or the creation of a small electrical gradient from one end to the other end, or side to side, of the bioreactor for use in electrical stimulation of cellular metabolism during induced new bone formation. This cyclic electrical stimulation can occur concurrent with, or not concurrent with, other mechanical or media changes to the forming, or formed, extracellular matrix containing the cells being manipulated to form new bone or bone-like tissue(s).

One aspect of the present invention is practiced by sterilizing all aspects of the bioreactor (tubing, fittings, valves, reagent (solution) containers, filters, sampling ports, bioreactor components, etc.).

Figure 1:
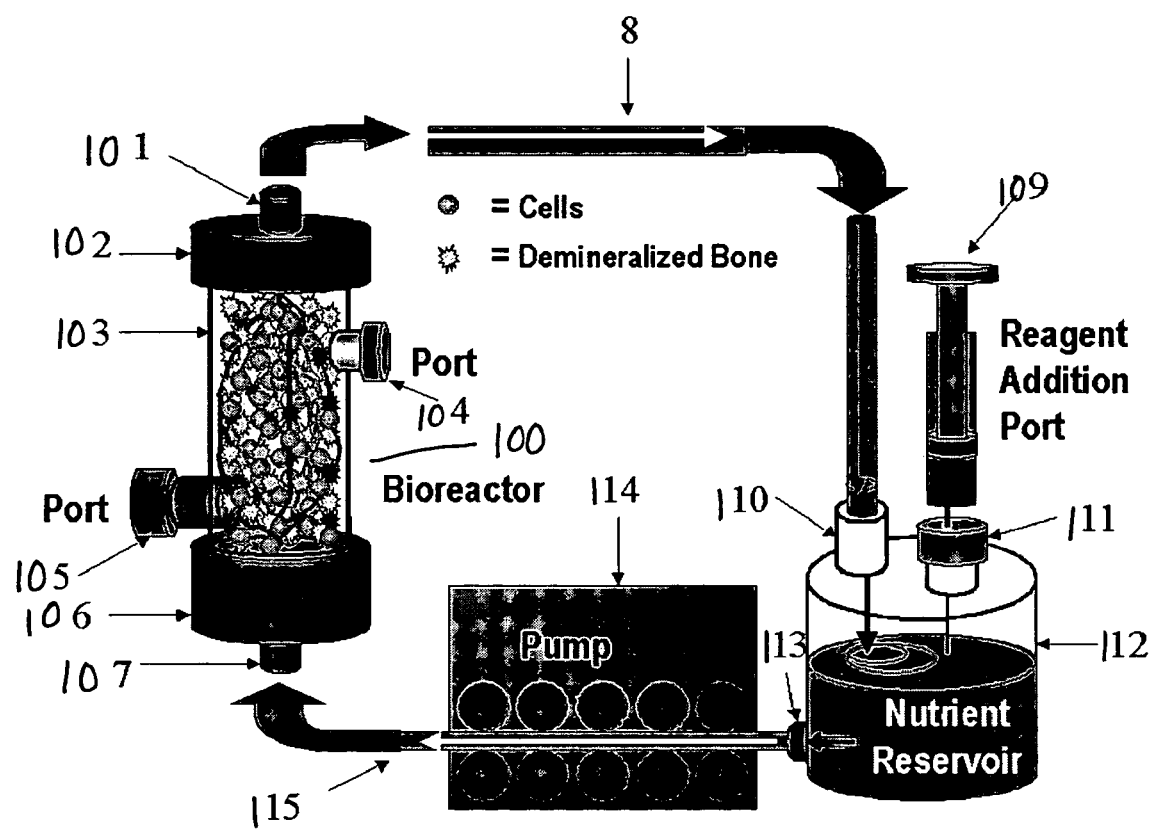
FIG. 1 illustrates a broad overview of a suitable hollow fiber bioreactor system to be used in the in vitro growth of tissue suitable to the formation of bone and bone forming tissue formed thereby.

The bioreactor 100 as shown in FIG. 1 illustrates an example of a hollow fiber bioreactor system of the present invention. The bioreactor 100 as set forth in FIG. 1 is aseptically assembled such that the hollow fibers 120 are connected to the inlet end-plate 106 and drawn through the tubular vessel 103 of the bioreactor 100 allowing the tubular vessel 103 of the bioreactor to be attached to the inlet end-plate 106 forming a water-tight seal. The non-connected end of the hollow-fibers 120 is then carefully attached to the outlet end-plate 102 forming a water-tight seal. Once the bioreactor is assembled, the ground demineralized bone can be rehydrated, if not already done so, and cells added via the injection ports 104 and 105. The bioreactor 100 is attached to at least one inlet port 107 and at least one outlet port 101 and the flow of nutrient solution from the nutrient reservoir 112 through the hollow fibers is initiated. The nutrients are delivered from the nutrient reservoir 112 through a noncytotoxic and non-hemolytic tubing 115 connected to the outlet port of nutrient reservoir 113 and the inlet port of the bioreactor 107. The flow is initiated and maintained in manners known in the art, but is preferably conducted centrifugal forces or a pump 114, such as a peristaltic pump, sufficient to cause the flow of media and waste products through the bioreactor 100. A pump 114 is preferably used to control the flow rate of the nutrients. Initiation of flow of nutrient solutions is important in that the cells contained in the bioreactor are labile to nutrient deprivation and thus the time between addition of cells to the bioreactor and initiation of nutrient solution flow should not exceed a time in which the specific cell population in the nutrient solution used to pack them becomes depleted of nutrients or changes pH to an extend that the cells become metabolically stressed. Additional reagents may added through a reagent addition port 109 as described above. Moreover, the waste generated from the bioreactor is removed through a tubing 108 connected to the outlet port 101 of the bioreactor 100 and the inlet port 110 of the nutrient reservoir 112. The eluent of medium from the bioreactor may be monitored to assess for proteins associated with bone formation, waste products, and nutritional capacity of the cells and demineralized bone, as described. The medium may also be recycled and recirculated into the nutrient reservoir 112 through a recycling inlet port 110. The nutrient solution in the nutrient reservoir 112 may be changed through the reagent addition port 109. One skilled in the art would appreciate when the nutrient solution should be changed. Preferably, the nutrient solution is changed at least once a week.

Figure 2:
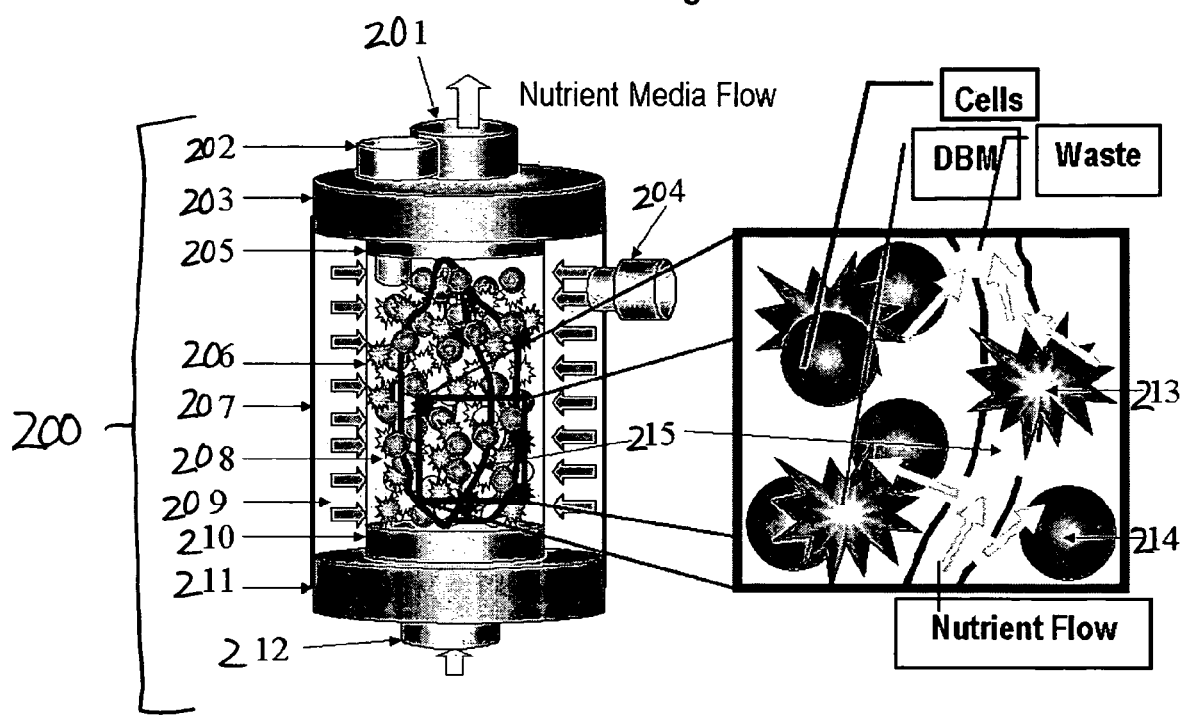
FIG. 2 illustrates the nutrient delivery and waste removal via hollow fibers of a suitable bioreactor within the scope of the present invention.
Figure 3:
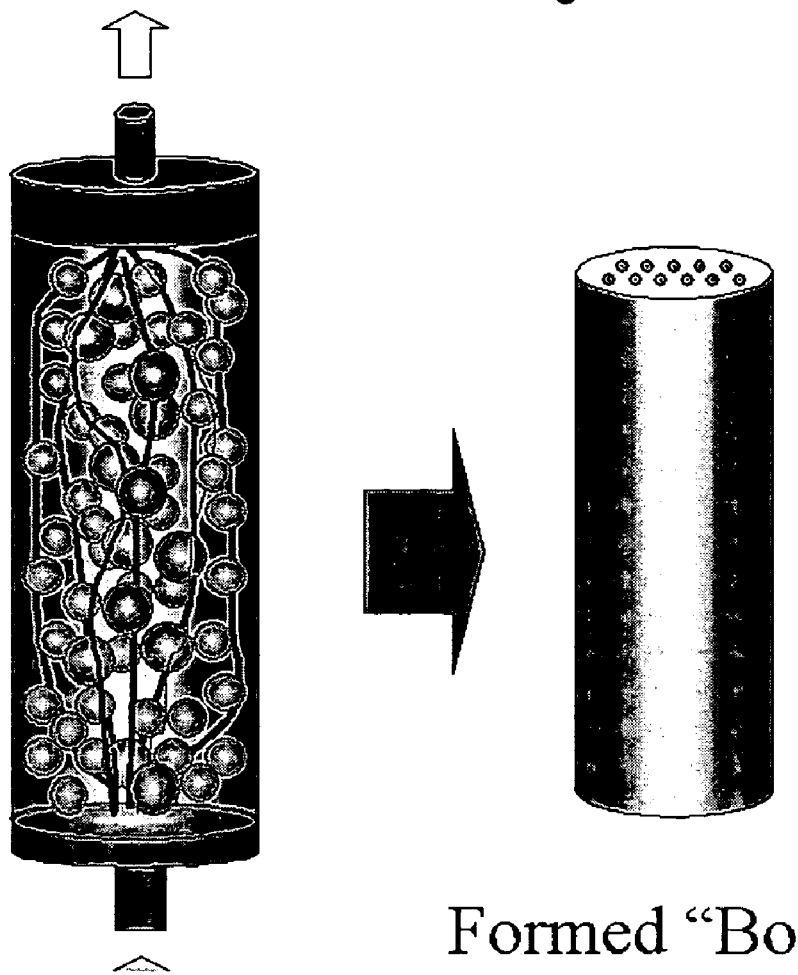
FIG. 3 illustrates "bone plug" formation in a bioreactor filled with DBM and cells.

Referring to FIG. 2, the nutrient delivery and waste removal via hollow fibers of a bioreactor 200 of the present invention is depicted. The bioreactor 200 is aseptically assembled such that the hollow fibers 215 are connected to the inlet end-plate 210 and drawn through the tubular inner chamber 208 of the bioreactor allowing the tubular inner chamber 206 of the bioreactor 200 to be attached to the inlet end-plate 210 forming a water-tight seal. The ground demineralized bone is added into the inner-most volume of the inner vessel 206 before or following rehydration until it fills the inner-most volume. If the ground demineralized bone is rehydrated prior to or concurrent with the addition to the inner-most volume, it is mixed with the cells to be used at an appropriate seeding density, i.e. number of cells/unit volume of extra-particle space. If the ground demineralized bone is not rehydrated prior to addition to the inner-most volume, the bone will need to be rehydrated prior to addition of cells once the bioreactor is fully assembled. The non-connected end of the hollow-fibers 215 is then carefully attached to the outlet end-plate 205 forming a water-tight seal. This inner chamber 206 is now ready for insertion into the outer chamber 209 component of the bioreactor 200. This is accomplished by sliding the outer most diameter of one of the end-plates 211 through the internal lumen of the outer chamber 209 until the remaining end-plate 203 can form a water-tight seal with the inner diameter of the outer chamber 209. As an alternative method, the assembled inner chamber 206 can simply be inserted into the outer chamber 209 by guiding (pressing) the end-plates, 203 and 211, into the guide holes present in the inner faces of the outer chamber 209. Once the bioreactor is assembled, the ground demineralized bone can be rehydrated, if not already done so, and cells 214 may be added via the injection ports, 202 or 204. The flow of the nutrients would enter via at least one inlet port 212 and exit through at least one outlet port 201.

The deformable wall of the inner chamber of the bioreactor may be constructed out of a flexible permeable barrier and a fine deformable mesh that can be molded to a specific shape as needed. The flexible permeable barrier is mechanically supported by a fine mesh, which is present either on the inside or the outside of the flexible permeable barrier. The flexible permeable barrier is made of any suitable resorbable or non-resorbable membrane, such as those comprising polydioxanone, polylactide, polyglactin, polyglycolic acid, polylactic acid, polyglycolic acid/trimethylene carbonate, cellulose, methylcellulose, cellulosic polymers, cellulose ester, regenerated cellulose, pluronic, collagen, elastin, or mixtures thereof. The fine mesh is suitably made up of sterilizable materials, such as stainless steel, titanium, plastic polymer, nylon polymer, braided collagen, and silk polymer, but must be capable of deforming to any desired shape. The fine mesh may have any suitable pore size dictated by the desired bone plug properties. For example, suitable pore sizes for the mesh is between about 0.1 to 10 mm and, preferably, 1-5 mm. The deformable wall may be made to be permeable for some metabolites and not others. For example, the deformable wall may be made to not be permeable to small or large molecular weight metabolites. In particular, a small molecular weight metabolite would fall within the range of 0.001 -25 kDa, preferably 0.1-2.5 kDa. A larger molecular weight metabolite would fall within the range of 25-200 kDa, preferably 25-50 kDa. The deformable wall may further be constructed to allow for its use in the bioreactor of the present invention. For example, the tensile properties of the deformable wall should make it capable of deforming under the cyclic negative and positive pressure, such as between 10-30mmHg. The mesh used to construct the deformable wall preferably will conduct an electrical current. The resorbable or non-resorbable hollow fibers can be used to deliver nutrients and remove waste for the inner chamber. The deformable inner chamber can be contained within a nondeformable outer chamber. The cyclic application of positive and negative pressures to the deformable wall of the inner chamber of the bioreactor to be used in the in vitro growth of bone or bone-like tissue serve to transform this bone or bone-like tissue into bone following transplantation into a recipient.

Figure 5:
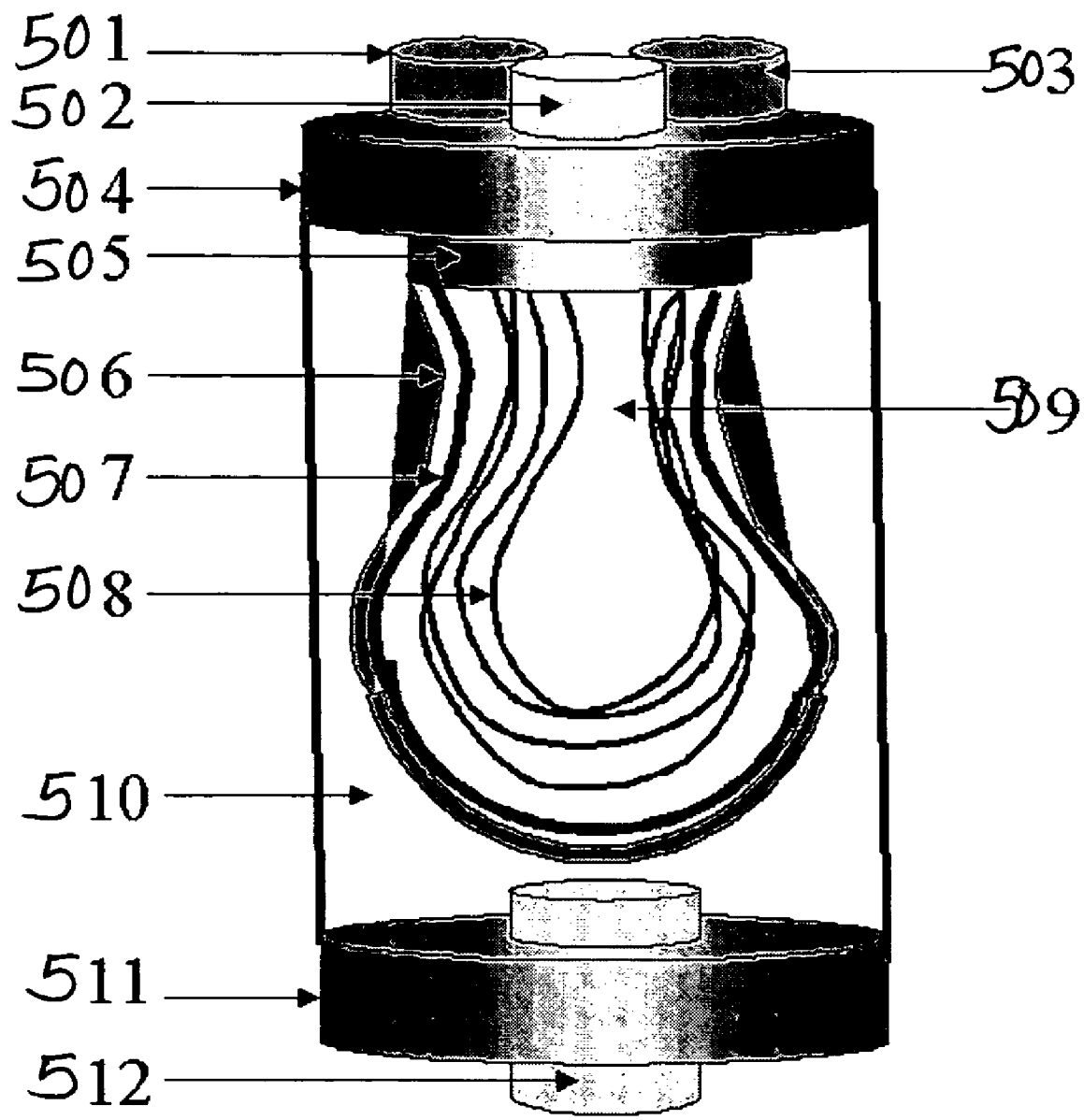
FIG. 5 depicts another suitable hollow fiber bioreactor within the scope of the present having an inner deformable chamber.
Figure 6:
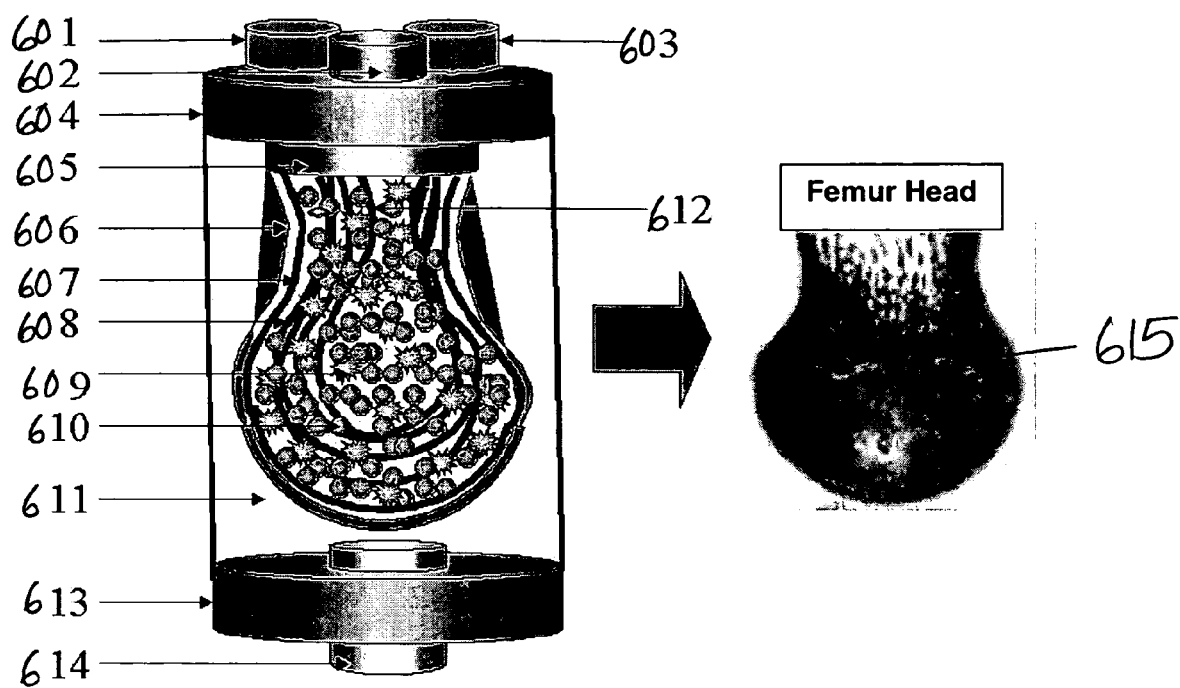
FIG. 6 depicts femoral head formation in a hollow fiber bioreactor made according to the method of the present invention.

Inlet and outlet ports of the outer chamber can deliver nutrients and remove waste for this deformable chamber (FIGS. 5 and 6). For example, FIG. 5 illustrates a hollow fiber bioreactor with an inner deformable chamber 509, wherein the deformable wall is comprised of a flexible permeable barrier 507 and a fine mesh 506. The bioreactor may contain one outer chamber 510 and one inner deformable chamber 509. The outer chamber 510 is closed by two end-plates 504 and 511 by means suitable for closing the chamber, such as an annular groove. The inner deformable chamber 509 is closed by one end-plate 505. The flexible permeable barrier 507 (non-resorbable membrane or resorbable membrane) and a fine mesh 506 are sealed to the plate 505 of the inner deformable chamber 509. The inner deformable chamber 509 can be deformed to the desired shape using a deformable metal mesh 506. At least one inlet 512 and at least one outlet 502 port is connected to the outer chamber 510 and are used for the nutrient delivery and waste removal in the outer chamber 510. Nutrient delivery and waste removal in the inner chamber 509 employ the use hollow fibers 508 connected to the at least one inlet 501 and at least one outlet 503 port on the outer chamber cover 504 and inner chamber cover 505.

FIG. 6 illustrates a femoral head formation using a hollow fiber bioreactor 600 of the present invention. The fine mesh 606 is deformed to the shape of a femoral head 615. A permeable membrane 607 is lined inside of the fine mesh 606. A mixture of demineralized bone materials 609 and cells 610 is added into the inner chamber 612 along with the hollow fibers 608 dispersed in the mixture of demineralized bone materials 609 and cells 610. The ends of hollow fibers 608 are connected to the two ports, inlet 601 and outlet 603, for nutrient delivery and waste removal from the inner chamber 612. The permeable membrane 607 and fine mesh 606 are sealed to the end-plate 605 of the inner chamber 612. The end-plate 605 of the inner chamber 612 is connected to the end-plate 604 of the outer chamber 611 through an annular groove: The nutrient is delivered into the out chamber through the inlet port 614 and the waste is removed from the outer chamber 611 through the outlet port 602.

The nutrient medium provided and the flow rate of this nutrient medium will vary depending on cell type added to the bioreactor, the packing density of the demineralized bone, presence/absence of a pre-added "extracellular matrix", and numbers and kinds of hollow fibers contained within the inner vessel of the bioreactor. Nutrient flow will continue until such time as it has been previously determined that the appropriate matrix (structure) has been obtained. At this time, the bioreactor is aseptically dismantled and the bone or bone-like structure aseptically removed for further use.

The formed new bone can consist of a nonmineralized and nonload-bearing osteoid-like material that will mineralize when transplanted into a heterotopic or orthotopic site in a patient or a partially mineralized and partially load-bearing osteoid material that will further mineralize when transplanted into a patient. Given time, it is also possible to produce an almost completely mineralized bone-like tissue that will be load-bearing when implanted clinically.

In another aspect of the invention, the demineralized ground bone and bone-forming cells may form an extracellular matrix that is capable of forming bone when implanted in a patient. In this manner, the demineralized bone and cells may be gelled in a viscous material and have non-loading bearing implantable material that will form in vivo similar to the in vitro bone-forming process described above.

Figure 7:
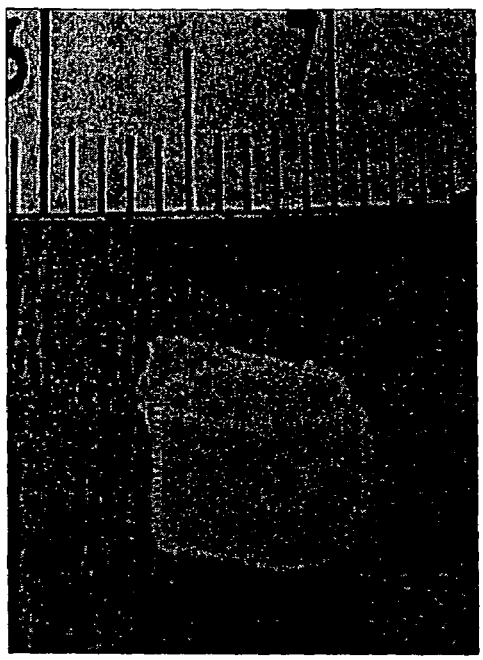
FIGS. 7A and 7B depict representative "bone plugs" generated in the hollow fiber bioreactor of the present invention. The dashed lines are intended for illustration purposes only. The histological analysis of these representative "bone plugs" was further depicted in FIGS. 11 to 14.
Figure 7:
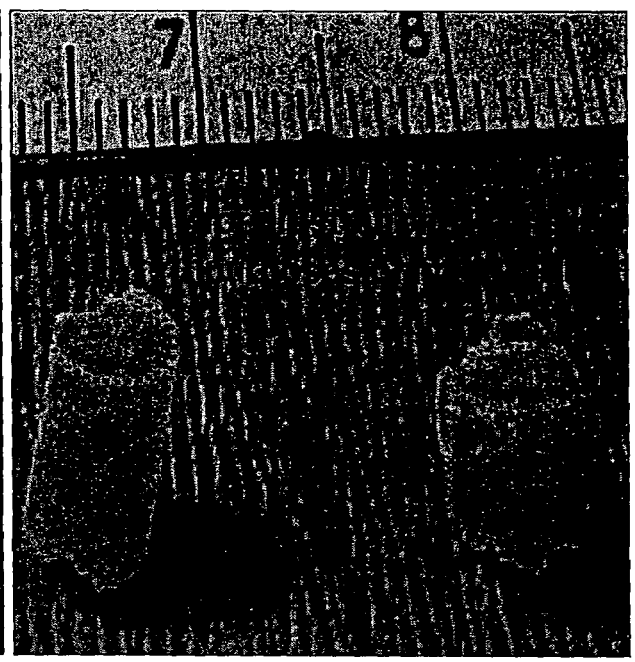

The bone, bone-like tissue, and extracellular matrix made according to the present invention is suitable for transplantation into a patient in need thereof. As one having ordinary skill in the art would appreciate, the bone, bone-like material or tissue, and extracellular matrix can be made into a desired shape that the body will remodel into the appropriate bone when implanted into a patient in some clinical application. For example, as shown in FIGS. 7A and 7B, bone plugs formed in bioreactors of the present invention can have varying shapes and sizes. In particular, the bone plugs depicted in FIGS. 7A and 7B were generated after 4 weeks of incubation of ground demineralized bone particles and human fibroblasts in the bioreactor.

Moreover, the bone, bone-like tissue, and extracellular matrix may be further treated prior to implantation in manners known in the art. For example, these materials may be acellularized using known methods prior to implantation. Preferred methods of acellularization include, but are not limited to, methods described in U.S. patent application Ser.

Nos. 09/528,371 and 09/660,422, which are hereby incorporated in their entirety. The acellularized bone, bone-like tissue and extracellular matrix is within the scope of the present invention. In addition, these acellularized may be recellularized by known methods either in vitro or in vivo. Alternatively, any residual resorbable hollow fibers present in the bone, bone-like tissue, or extracellular matrix may be removed using hydrolytic enzymes, such as cellulase, chitinase, collagenase, elastase, proteases such as chymotrypsin, trypsin, ficin, papain and/or specific enzymes that are capable of degrading the polymers comprising the resorbable and non-resorbable hollow fibers and dialysis films. Other known methods of processing bone prior to implantation are further within the scope of the present invention.

EXAMPLES

The following examples are for purposes of illustration only and are not intended to limit the scope of the appended claims.

Example 1

Growth of New Bone Using a Sample Inner Vessel Consisting of Dialysis Membrane Tubing in a Circulating Solution of Nutrient Solution Dialysis tubes (Spectrum, Spectra/Por) made with different membrane pore sizes (MWCO 10,000-25,000) and different material (regenerated cellulose or cellulose ester) were used for musculoskeletal bone tissue regeneration. The hydrogen peroxide in sterile dialysis tubes was removed and the tubes were soaked in tissue culture media for 1-2 hours in order to remove all remnants of hydrogen peroxide. Demineralized bone matrices were weighed aseptically and hydrated with cell suspension (human dermal fibroblasts or human periosteal cells) in RPMI 1640 tissue culture medium. The DBM and cell mixtures were introduced into dialysis tubes and the tubes were incubated in culture media containing 2% FBS, 50 µg/ml L-ascorbic acid, 1 µM dexamethasone, and 50 mM beta-glycerolphosphate. The dialysis system was incubated either under static (that means the dialysis tubes are incubated in a media container), stirred dynamic (that means the dialysis tubes are incubated in a media container which stays on stir plate to give constant mixing speed), or fluid-flow dynamic (that means the dialysis tubes are incubated in a media flow chamber which controls the media flow rate for dialysis tubes by peristaltic pump) conditions. The culture media were replaced by fresh media once a week to keep sufficient nutrients for cell growth and differentiation.

Figure 10:
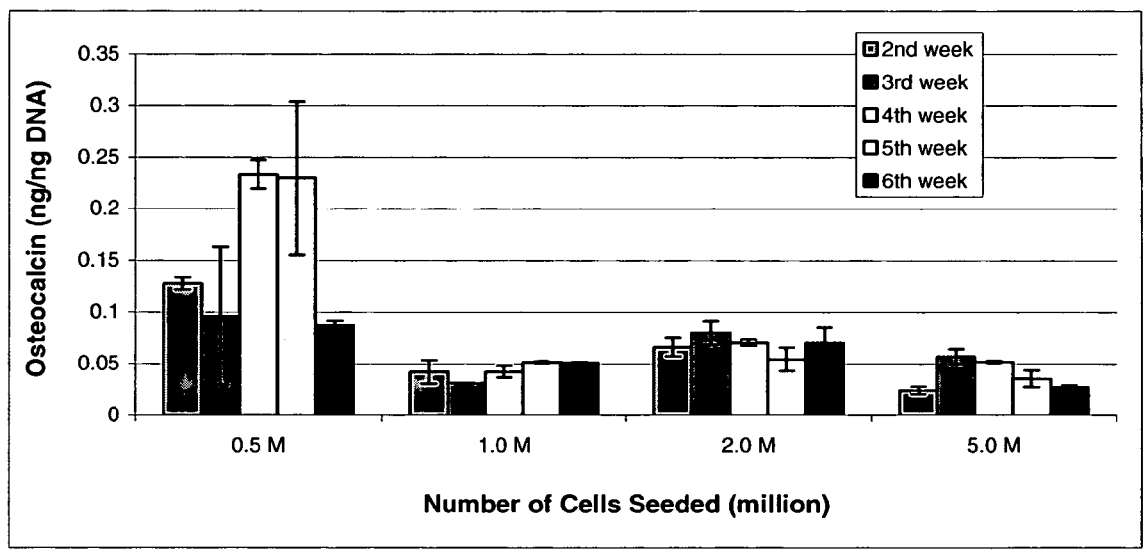
FIG. 10 illustrates the osteocalcin levels (ng/ng DNA) for various cell seeding densities (0.5, 1.0, 2.0, and 5.0 million fibroblast cells per 100 mg of DBM) on the $2^{nd}$, $3^{rd}$, $4^{th}$, $5^{th}$, and $6^{th}$ week of incubation.

During various time of incubation (1-7 weeks), the culture media were taken out from the containers for osteocalcin quantitation by ELISA, the tissues from the dialysis tubes were taken out for histology analysis, alkaline phosphatase quantitation, percentage of calcium quantitation, and double strand DNA quantitation. The samples of culture media were taken out from bioreactor each week for osteocalcin quantification by ELISA. FIG. 10 shows the time course of the bone protein, osteocalcin, levels for different cell seeding densities and identifies that the osteocalcin levels in the culture media increased significantly for the first 4 weeks and were more consistent after fourth week. Similarly, the osteocalcin levels normalized by the amount of DNA in the bone plugs generated in the bioreactor was also calculated based on the various cell seeding densities and incubation time. As shown in FIG. 10, the lowest seeding density (0.5 million fibroblast cells per 100 mg of DBM) showed the highest osteocalcin level from second to fifth week of incubation.

Figure 8:
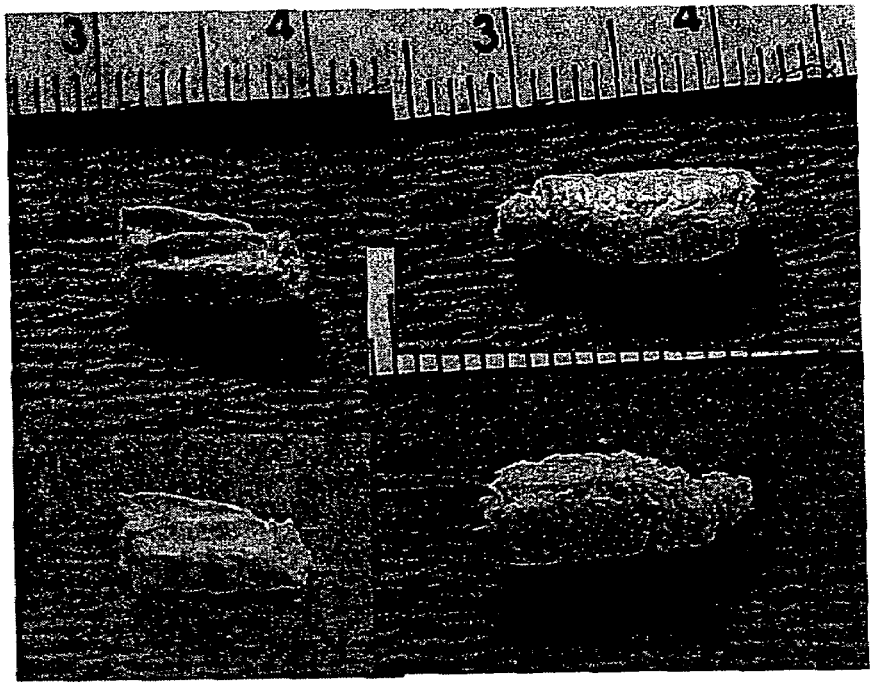
FIGS. 8A-D illustrate representative "bone plugs" generated in the bioreactor that are subsequently freeze-dried. The shapes of the "bone plugs" reflect the shape of the deformable inner vessel of the bioreactor.
Figure 9:
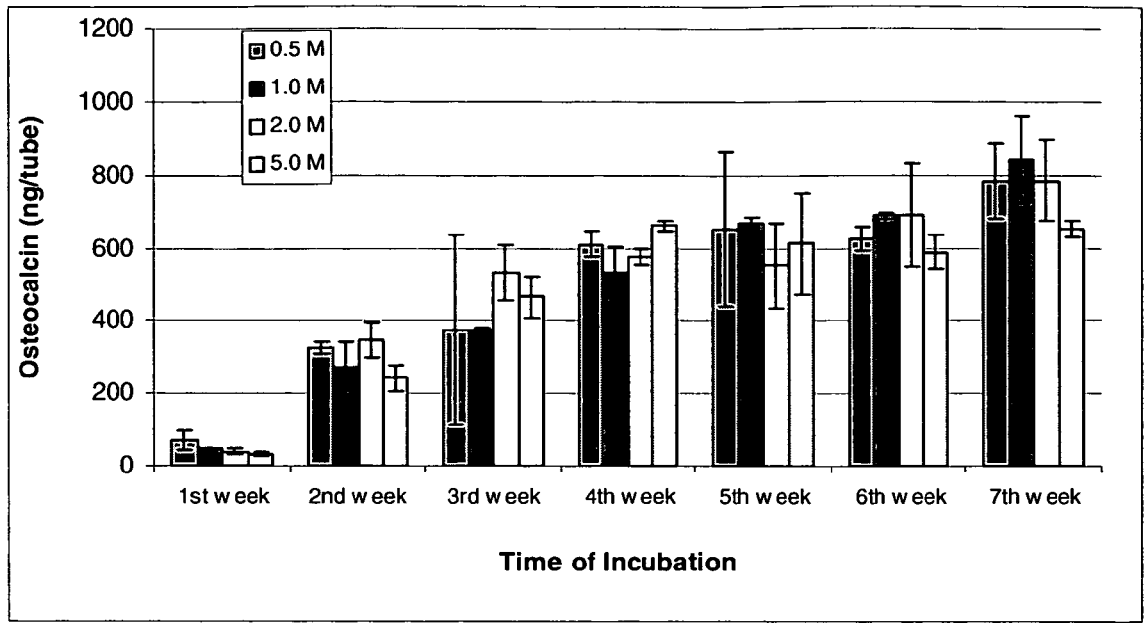
FIG. 9 illustrates the time course of the osteocalcin levels (ng/tube) for different cell seeding densities (0.5, 1.0, 2.0, and 5.0 million fibroblast cells per 100 mg of DBM) over an incubation period of 7 weeks.

Various bone plugs produced according to this example were further examined. Specifically, some of the bone plugs formed according to this example are depicted in FIGS. 7A and 7B, which indicates the various shapes and sizes available to the person performing the invention. Additionally, FIG. 8 illustrates the bone plugs generated in the bioreactor that are subsequently freeze-dried. The shapes of these bone plugs reflect the shape of the deformable inner vessel of the bioreactor. FIGS. 11A-C and 12A-C illustrate the histological analysis of a bone plug generated in a bioreactor at 200× and 400× magnification, respectively. The "bone plug" generated in bioreactor was embedded and sectioned and the sections were stained with the Alizarin Red, H&E, and Masson's Trichrome methods. The Alizarin Red staining revealed the calcium deposition in newly formed extracellular matrix. H&E staining revealed the changes in fibroblast morphology and new extra-cellular matrix (ECM) production that appeared to be "osteoid" formation. Masson's Trichrome staining suggested that the newly formed extracellular matrix contained significant quantities of collagen.

FIGS. 13A-D illustrate the H&E staining of a bone plug generated in a bioreactor and an analogous bone plug generated from heterotopic implantation of DBM in a nude mouse (400× magnification). The new bone growth in a bioreactor (FIGS. 13A and 13B) of the present invention after 4 weeks incubation was compared to the new bone growth in a nude mouse (FIGS. 13C and 13D) 4 weeks after DBM implantation. The changes in fibroblast morphology and new extracellular matrix production appeared on both samples.

FIGS. 14A-B illustrate the Mason's Trichrome staining of a bone plug generated in a bioreactor (FIG. 14A) and an analogous bone plug generated from heterotopic implantation of DBM in a nude mouse (FIG. 14B) (400× magnification). Significant amounts of new extracellular matrix were produced around cells and stained as collagen fibril for both "bone plug" generated in a bioreactor and explants from a nude mouse.

FIG. 15 illustrates the alkaline phosphatase activity for bone plugs generated in a hollow fiber bioreactor with various cell seeding densities. The group at a cell seeding density of $1 \times 10^7$ human periosteal cells per 500 mg of DBM showed significantly higher alkaline phosphatase activity than other groups tested.

Example 2

Growth of New Bone Using a Prototypic Hollow-Fiber Containing Bioreactor

The bioreactor was constructed from glass tubing (inner diameter, 5 mm; length, 50 mm) and contained forty porous regenerated cellulose hollow fibers (outer diameter, 216 µm; inner diameter, 200 µm; MWCO of 18,000; Spectra/Por®; Spectrum Laboratories, Inc.; Laguna Hill, Calif.). The hollow fibers were embedded in biomedical grade silicon rubber (Nusil Silicone Technology, Carpenteria, Calif.).

To determine the optimal cell seeding density in the bioreactor system, human periosteal (HPO) cells were inoculated into the bioreactor at various cell density of $0.5 \times 10^6$, $1 \times 10^6$, $5 \times 10^6$, and $1 \times 10^7$ cells with DBM (1.5 cc or 500 mg). The culture medium used comprises Dulbecco's modified Eagle's medium (DMEM) supplemented with antibiotics, ascorbic acid, beta-glycerophosphate, dexamethasone, and 2% fetal bovine serum (FBS). Two hundred and fifty ml of cell culture medium was recirculated with a medium flow rate of approximately 5 ml/min. After inoculation, the bioreactors were perfused using a peristaltic pump and maintained in a 5% $CO_2$/

Figure 16:
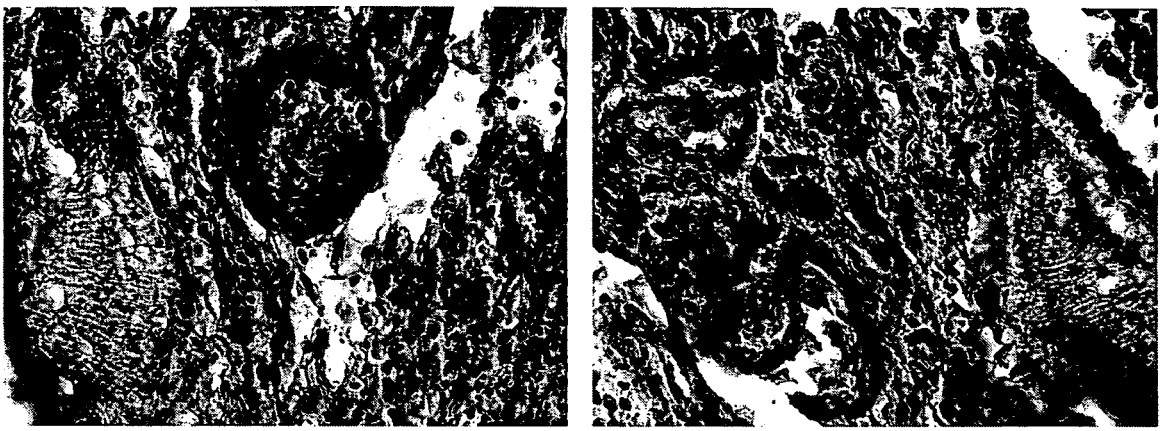

95% air incubator. After 5 days, the samples of cells with DBM were removed and in vitro alkaline phosphatase assay was performed. FIG. 16 represents the various cell seeding densities of HPO cells and the activities of alkaline phosphatase from the in vitro alkaline phosphatase assay. These data demonstrate that HPO cells at a density of $1\times10^7$ cells have significantly higher alkaline phosphatase activities than other groups with different cell seeding densities tested.

To study the growth of new bone or bone-like tissue using hollow-fiber bioreactor system, the bioreactor was inoculated with $1\times10^7$ cells and DBM (1.5 cc or 500 mg) through either end into the extracapillary space of the bioreactor. Dulbecco's modified Eagle's medium (DMEM) supplemented with antibiotics, ascorbic acid, beta-glycerophosphate, dexamethasone, and 2% fetal bovine serum (FBS) was used as culture medium throughout the experiments. Culture medium was changed weekly. Two hundred and fifty ml of cell culture medium was recirculated with a medium flow rate of approximately 5 ml/min. Diffusive nutrient supply and removal of metabolic waste products across the membrane of hollow fiber was advanced by constantly recirculating culture medium through the system using a peristaltic pump maintained in a 5% $CO_2$ incubator. After 3 weeks, samples were taken from the bioreactors, fixed in neutral buffered formalin, embedded in paraffin and sectioned. Sections were stained with Haematoxylin & Eosin. The results were illustrated in FIGS. 16A-B showing H&E stained large cuboidal-shaped cells with deposition of collagen and organic bone matrix at 400× magnification.

Each of the patents and publications cited herein are incorporated by reference herein in their entirety. It will be apparent to one skilled in the art that various modifications can be made to the invention without departing from the spirit or scope of the appended claims.

What is claimed is:

1. A method of growing new bone or bone tissue under in vitro cell culture conditions comprising,
    providing a bioreactor, ground demineralized bone, nondemineralized bone, and bone-forming cells, wherein the nondemineralized bone comprises at least one of nondemineralized bone fibers and nondemineralized bone particles,
    placing the ground demineralized bone, nondemineralized bone, and the bone-forming cells in the bioreactor, and
    providing a nutrient solution comprising nutrients and oxygen for the bone-forming cells,
    causing the nutrient solution to flow into, through, and out of the bioreactor containing the ground demineralized bone, nondemineralized bone, and the bone-forming cells to bring the flowing nutrient solution into contact with the bone-forming cells,
    wherein nutrients and oxygen in the flowing nutrient solution are at sufficient concentrations to permit differentiation of the bone-forming cells into bone or bone tissue in the bioreactor.

2. The method of claim 1, wherein the bone-forming cells are selected from the group consisting of stem cells, fibroblast cells, periosteal cells, chondrocytes, chondroblasts, osteocytes, pre-osteoblasts, osteoblasts and genetically modified cells.

3. The method of claim 2, wherein the bone-forming cells are osteoblasts, chondrocytes, and chondroblasts.

4. The method of claim 1, wherein the ground demineralized bone is in the form of particles.

5. The method of claim 4, wherein the ground demineralized bone is freeze-dried.

6. The method of claim 5, wherein the ground demineralized bone is rehydrated prior to being placed in the bioreactor.

7. The method of claim 5, wherein the ground demineralized bone is rehydrated after being placed in the bioreactor.

8. The method of claim 4, wherein the ground demineralized bone particles have an average size of about 50 microns to about 4 mm.

9. The method of claim 4, wherein the ground demineralized bone particles haven an average size of about 250 microns to about 710 microns.

10. The method of claim 1, wherein the ground demineralized bone is in the form of fibers.

11. The method of claim 10, wherein the demineralized ground bone fibers have a width of about 0.1 mm to about 0.5 mm, a thickness of about 0.05 mm to about 0.5 mm, and a length of about 1 mm to about 500 mm.

12. The method of claim 1, wherein the bone-forming cells synthesize and secrete bone or bone tissue matrix.

13. The method of claim 12, wherein the bone matrix is viscous.

14. The method of claim 1, further comprising adding collagen or hyaluronin to the ground demineralized bone, nondemineralized bone, and bone-forming cells in the bioreactor.

15. The method of claim 1, wherein the nutrient solution comprises at least one of Dulbecc's Modified Eagle's Medium, fetal bovine serum, L-ascorbic acid, antibiotics, dexamethasone, beta-glycerolphosphate, glucose, glutamine, amino acid supplements, glutathione-ethyl ester, antioxidants, caspase inhibitors, cations, and anions.

16. The method of claim 1, wherein the nutrient solution is introduced into the bioreactor through resorbable hollow fibers.

17. The method of claim 16, further comprising implanting the new bone or bone tissue into a recipient, and degrading the resorbable hollow fibers using hydrolytic enzymes prior to implantation of the bone or bone tissue.

18. The method of claim 16, further comprising introducing growth promoting factors through the resorbable hollow fibers into the bioreactor and degrading the resorbable hollow fibers thereby leaving channels through the bone or bone tissue, wherein the new bone or bone tissue having the channels is implanted into a recipient.

19. The method of claim 18, further comprising delivery of growth factors through the channels in the implanted bone or bone tissue to promote angiogenesis.

20. The method of claim 1, wherein metabolic waste products are produced by the bone-forming cells in the bioreactor, and wherein the metabolic waste products are removed from the bioreactor through resorbable hollow fibers.

21. The method of claim 1, wherein at least one growth factor is introduced into the bioreactor, and the ground demineralized bone, the nondemineralized bone, and the bone-forming cells are contacted with the growth factor.

22. The method of claim 21, wherein the growth factor is a vascular endothelial growth factor.

23. The method of claim 1, wherein the ratio of mass of ground demineralized bone to nondemineralized bone is about 1:1 to about 20:1.

24. The method of claim 1, further comprising implanting the new bone or bone tissue into a recipient, wherein the bone-forming cells are autogenic, allogenic, or xenogenic with respect to the recipient.

25. The method of claim 1, wherein the bone-forming cells are added to the bioreactor after the ground demineralized bone and after the nutrient solution have been added to the bioreactor.

26. The method of claim 1, wherein the bone-forming cells are placed in the bioreactor prior to placing the ground demineralized bone in the bioreactor.

27. The method of claim 1, wherein at least one differentiation factor is introduced into the bioreactor, and the ground demineralized bone, the nondemineralized bone, and the bone-forming cells are contacted with the differentiation factor.

28. The method of claim 27, wherein the differentiation factor is a bone morphogenetic protein.

29. The method of claim 1, wherein at least one growth factor and one differentiation factor are introduced into the bioreactor, and the ground demineralized bone, the nondemineralized bone, and the bone-forming cells are contacted with the growth factor and differentiation factor.

30. The method of claim 29, wherein the growth fact is a vascular endothelial growth factor and the differentiation factor is a bone morphogenetic protein.

* * * * *

UNITED STATES PATENT AND TRADEMARK OFFICE
CERTIFICATE OF CORRECTION

PATENT NO. : 7,494,811 B2
APPLICATION NO. : 10/835529
DATED : February 24, 2009
INVENTOR(S) : Lloyd Wolfinbarger, Jr. et al.

It is certified that error appears in the above-identified patent and that said Letters Patent is hereby corrected as shown below:

Column 21, line 2, after "are placed" and before "the bioreactor", please replace "in" with "into".

Column 22, line 6, after "the growth" and before "is", please replace "fact" with "factor".

Signed and Sealed this

Twenty-first Day of July, 2009

JOHN DOLL
*Acting Director of the United States Patent and Trademark Office*